United States Patent [19]

Martin

[11] Patent Number: 5,549,558

[45] Date of Patent: Aug. 27, 1996

[54] SELF SHEATHING SAFETY NEEDLE

[76] Inventor: Robin P. Martin, 810 S. Texas Blvd., Weslaco, Tex. 78596-7054

[21] Appl. No.: 488,516

[22] Filed: Jun. 9, 1995

[51] Int. Cl.[6] ........................................ A61M 5/00
[52] U.S. Cl. ........................ 604/110; 604/198; 604/263
[58] Field of Search ................................. 604/110, 187, 604/192, 195, 198, 263

[56] References Cited

U.S. PATENT DOCUMENTS

| | | | |
|---|---|---|---|
| 4,813,940 | 3/1989 | Parry | 604/198 |
| 4,911,693 | 3/1990 | Paris | 604/192 |
| 4,985,021 | 1/1991 | Straw et al. | 604/263 X |
| 5,104,384 | 4/1992 | Parry | 604/192 |
| 5,312,370 | 5/1994 | Talonn et al. | 604/198 |
| 5,314,414 | 5/1994 | Hake et al. | 604/198 |

*Primary Examiner*—John D. Yasko
*Attorney, Agent, or Firm*—Bush, Moseley, Riddle & Jackson

[57] ABSTRACT

A self sheathing safety needle comprising a needle assembly (50), a needle guard (52), and an outer casing (54) is shown in exploded relation in FIG. 1 . Needle guard (52) has a locking tab (100) mounted on the free end of a spring finger or lever (98). Locking tab (100) is received within an internal track on outer casing (54) which has a cam lug (148) for effecting movement of locking tab (100) between a locked extended position of the needle guard (52) and an unlocked extended position of the needle guard (52) to permit retraction of the needle guard (52). Casing (54) is mounted for limited rotation on bearings (60, 62) on the hub (86) of the needle assembly (50) to effect movement of the locking tab (100) to an unlocked position. Stops (76, 78, 80, 82) on bearings (60, 62) limit relative rotation of casing (54) between locked and unlocked positions of needle guard (52) and locking tab (100). During injection, the end (104) of the needle guard (52) is always in contact with the patient, and the needle (50) is never exposed, thus unable to inflict an accidental needle-stick injury. When needle (50) is withdrawn from the patient, locking tab (100) automatically travels along track (145), and is cammed into a locked extended position by the cam lug (148) and associated adjacent surfaces.

20 Claims, 5 Drawing Sheets

SELF SHEATHING SAFETY NEEDLE

FIELD OF THE INVENTION

This invention relates to medical equipment, and more specifically to safety needle devices for the injection or aspiration of a fluid.

BACKGROUND OF THE INVENTION

Today there presently still remains a very significant risk on the part of medical professionals, of obtaining on the job infections of HIV, HBV (Hepatitis B), and other serious blood borne diseases as the result of contaminated needle stick injury. Many inventions and devices have been invented and proposed to help solve this problem; however to date, there is still no device on the market that sufficiently and cost effectively brings a solution to this problem. Needle stick injuries continue to occur at an alarming rate. This problem is also of significant concern in the area of veterinary medicine, which also needs to be addressed. It is possible for many animal diseases to be transmitted to humans via a contaminated needle-stick injury, some of which can be quite serious and even fatal.

Many needle devices have been made heretofore that still expose the sharp needle point during some time of the operation of the device, thus still exposing the medical worker to accidental needle-stick injury. Other safety syringes have been marketed that utilize a safety shield which must be manually pulled over the exposed sharp needle point after an injection. These devices are not effective in prevention of accidental needle-stick injuries, because they do not shield the sharp needle point during one of the most likely times for a contaminated needle stick injury; immediately after an injection. They are also difficult and cumbersome to use. Some in fact even seem to increase the chance of injury.

U.S. Pat. No. 4,813,940 dated Mar. 21, 1989 shows an injection device in which a pair of telescoping sleeve members receive a needle with an inner sleeve member covering the needle in an extended position. The inner sleeve member is manually rotated for movement from a locked position preventing retraction of the sleeve member, and an unlocked position permitting retraction of the sleeve member for injection or aspiration of a fluid from the needle. The outer sleeve member or housing is secured to an inner member in which the base of a needle is press fitted. While relative rotation between the inner and outer sleeve members is provided for unlocking of the sheath, only a pin in a track restricts or stops the manual rotation of the inner sleeve member or sheath. The manual rotation of the sheath, particularly if gripped at the projecting end of the sheath adjacent the sharp needle end is undesirable and may result in failure particularly if a large rotative force is applied.

OBJECTS AND ADVANTAGES

It is a general object of my self sheathing needle to bring a suitable and cost effective solution over the prior art to this serious problem, both in health care and veterinary settings, and to provide a passive self sheathing safety needle designed to prevent accidental needle stick injuries.

It is another object of my self sheathing needle to provide a self sheathing needle that is easy to use and inexpensive to manufacture.

It is another object of my self sheathing needle to provide a passive device that takes a minimum of manipulation and teaching to use properly, as compared with prior art medical syringes and other injection safety devices, which are often difficult to manipulate and cumbersome to use.

It is a further object of my self sheathing needle to provide a self sheathing safety needle that will offer protection even when the needle is only partially injected.

It is another object of my self sheathing needle to never expose the dangerous sharp needle point, thus fully protecting the medical worker from accidental needle-stick injury, prior to, during, and after injection or aspiration.

Still further objects and advantages will become apparent from a consideration of the following description and drawings.

SUMMARY OF THE INVENTION

The present invention is directed particularly to a self sheathing needle in which an inner needle guard member or sheath is mounted in telescoping relation within an outer casing member for relative rotation between an extended locked position of the needle guard member and an extended unlocked position of the needle guard member. In the unlocked position of the needle guard member or sheath, the sheath may be moved to a retracted position by contact with a patient or object upon injection or aspiration of a fluid by the needle. The needle may be used more than once to permit first the drawing of the medication for injection, and then performing the injection procedure.

The outer casing member, preferably of a cylindrical shape, receives the inner needle guard member which is continuously urged to an extended position, and coacting guide means on the casing member and the needle guard member guide the needle guard member to an unlocked position upon manual rotation of the outer casing member. The guide means on the needle guard member includes a resilient spring finger having a locking tab on the extending free end of the spring finger. The locking tab is cammed radially by a ramp on the casing member for movement between locked and unlocked positions.

A needle assembly includes the hollow needle and a base for the needle. Additional coacting guide means on the base and the needle guard member operably connect the base and needle guard member for relative longitudinal sliding movement of the needle guard member while blocking relative rotational movement between the base and the needle guard member. The base includes a hub portion which has an outer arcuate bearing supporting the casing member for rotative movement upon manual rotation of the casing member. Stops are provided adjacent the bearing for limiting the rotation of the casing member at the extended locked position and the extended unlocked position of the needle guard member. Thus, separate stop means for blocking rotation of the casing member past the locked and unlocked extended positions of the needle guard member are provided to supplement the blocking by the locking tab. Such an arrangement provides a safety feature in the event of failure of a locking tab.

A compression spring constantly urges the needle guard member to an extended position. This results in the needle guard member always being in contact with the human patient or other object being injected, while the needle device is in actual operation. Thus, the sharp needle point is never exposed to the outside during use of the self sheathing needle thereof preventing accidental needle sticks or pricks.

The embodiment illustrated in the drawings is designed to be used with any type hypodermic syringe device, or any other device with a conventional luer lock fitting which may be used for introducing fluid into a human body or extracting any fluid or other material from a human body, during medical procedures in the health care setting, or similar procedures in the veterinary setting. However, the present invention may be utilized with a friction fit design such as would be used on the end of an insulin syringe, or other friction fit type syringe or device, in which the needle is installed with a friction fit.

Also, the present invention may be utilized in a blood collecting design, to be used with conventional blood collection systems that utilize a double sided blood collection needle with a threaded attachment to a blood collection needle holder.

Any of the various embodiments may be pre-installed with the hypodermic syringe or other device, or it may be installed manually prior to use by the medical worker.

Other objects, features, and advantages of the invention will become more apparent after referring to the following specification and drawings.

BRIEF DESCRIPTION OF THE DRAWINGS

Reference will now be made to the drawings, wherein like parts are designated by like numerals, and wherein.

DESCRIPTION OF THE INVENTION

Figure 1:
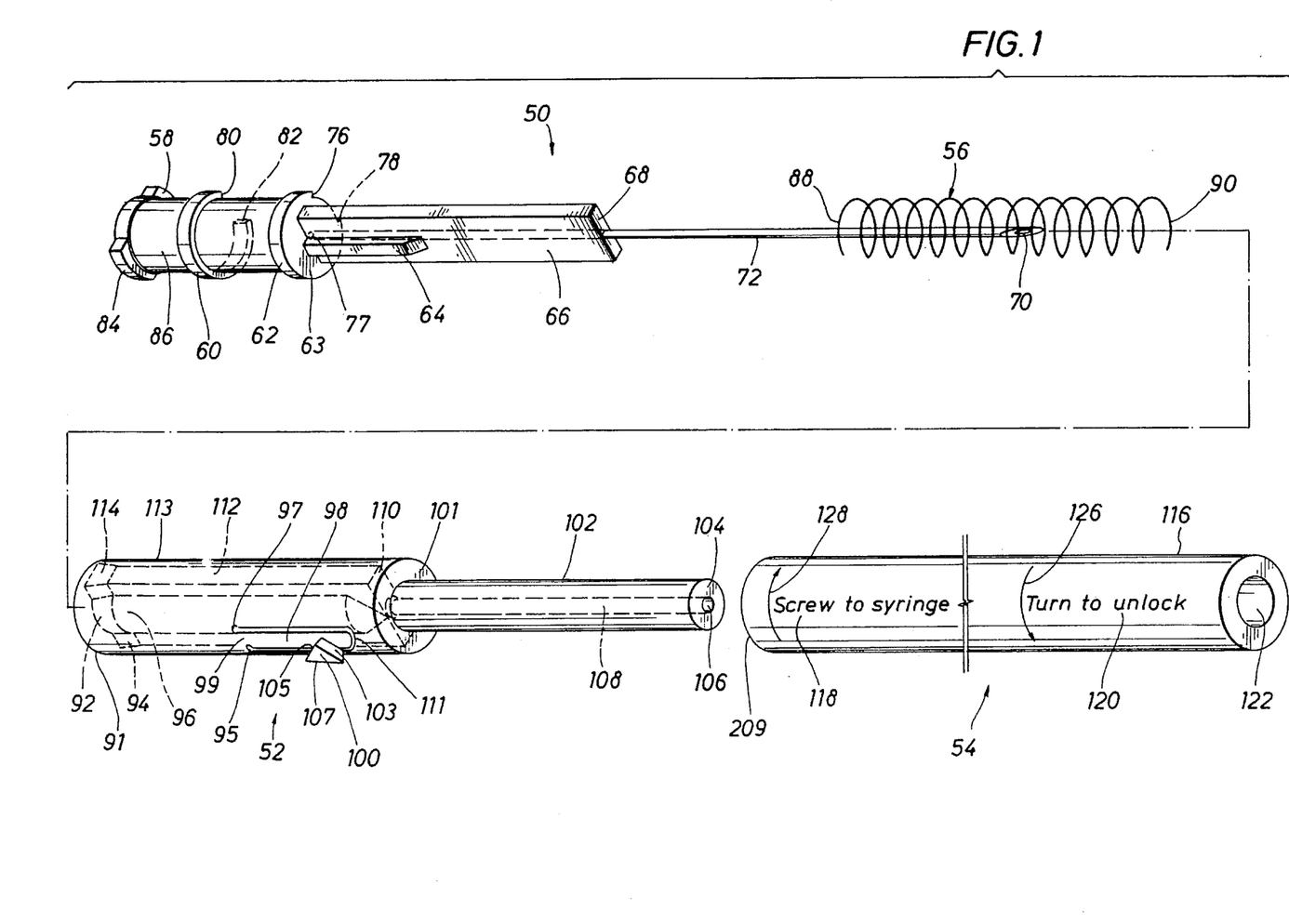
FIG. 1 is an isometric exploded view of the self sheathing needle comprising the present invention.

Referring now to the drawings for a better understanding of this invention and more particularly to FIG. 1, the self sheathing needle of this invention comprises a needle assembly 50, a compression spring 56, a needle guard member 52, and a casing member 54.

NEEDLE ASSEMBLY

Figure 2:
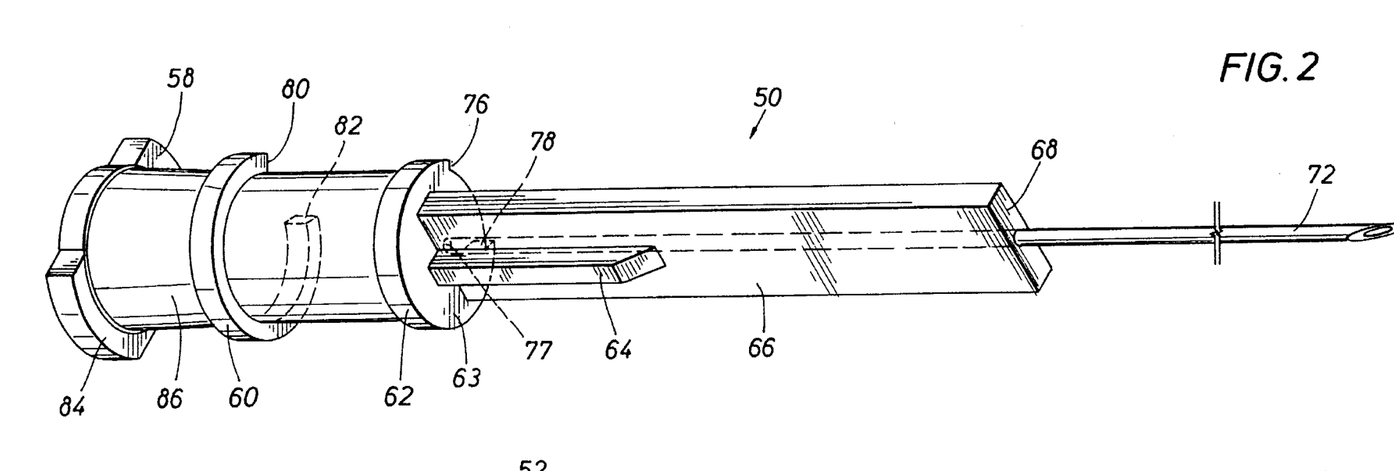
FIG. 2 is an enlarged isometric view of the needle assembly of the invention shown in FIG. 1.

Needle assembly 50 is shown in an enlarged view in FIG. 2. Referring to FIG. 2, needle assembly 50 comprises a hollow tapered needle hub or base 86, a rectangularly shaped sliding bar portion 66 secured to hub 86, and a hollow needle 72 having a hollow sharp needle point 70. Needle or needle shaft 72 can be made of any desired length, size, or gauge, generally out of a suitable metal, such as stainless steel. The remainder of needle assembly 50 can be made of any suitable plastic, common to disposable syringes, which is able to tolerate standard sterilization treatment prior to distribution. Needle assembly 50 can also be made of any other suitable materials, such as stainless steel or other metals when used in veterinary practices, or working with laboratory animals, where using a needle on multiple subjects is permissible. Any material that will fit the properties needed may be used.

Figure 7:
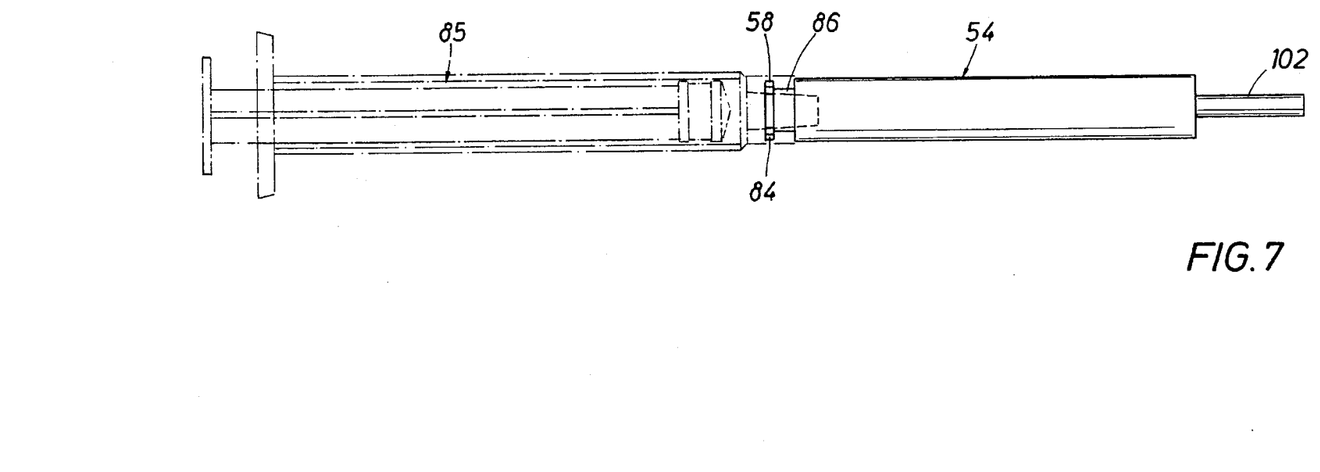
FIG. 7 is a plan view illustrating the connection of a luer lock syringe to the self sheathing needle of the present invention.

Attached to hub 86 are two arcuate projections or lugs 58 and 84. Projections 58 and 84 are diametrically opposed to each other, and are sized and shaped to engage the luer lock fittings of any conventional luer lock syringe or luer lock device such as shown at 85 in broken lines in FIG. 7. Hub 86 is hollow, and is of a tapered tubular shape to receive the male connector portion of the conventional luer lock syringe 85 as shown in FIG. 7, in a sealing frictional engagement. Spaced longitudinally on the outside surface of hub 86 are arcuate rotational bearings 60 and 62.

At the ends of bearing 60 are two opposing rotational safety stops 80 and 82 having flat surfaces. The surfaces of stops 80 and 82 form an inclined acute angle with the outer surface of hub 86. This inclined angle matches the angle at which stops 80 and 82 engage a rotational safety stop bar 202 at a pair of surfaces 204 and 206, as casing or casing member 54 rotates on bearings 60 and 62 as shown particularly in FIGS. 4 and 6.

Because of the inclined surfaces of stops 80 and 82, and the matching inclined surfaces 204 and 206 of stop bar 202; the harder that casing 54 is twisted either clockwise or counterclockwise, the tighter safety stops 80 and 82 are pushed into the angles formed at the junction of stop bar 202 with casing 54. This gives the entire assembly exceptional strength and stability against strong rotational forces which may be exerted while attaching my self sheathing needle to a conventional luer lock syringe.

Bearing 62 at the end of hub 86 is also provided with a pair of rotational safety stops 76 and 78, which are formed in similar fashion to stops 80 and 82, one stop being at each end of bearing 62. Stops 76 and 78 also are formed at inclined acute angles, and are matching with the inclined surfaces of stop bar 202 at safety stop surfaces 142 and 198. Second bearing 62 is not essential to my self sheathing needle, but will make it stronger and more stable when used.

The bottom inside surface of hub 86 has a small hole 77 as shown in FIG. 2 which is formed integrally with the inner end of hollow needle shaft 72. The inner end of hub 86 defines a planar surface 63 and rectangular sliding bar 66 is fixedly attached to surface 63. A rectangular reinforcing strip 64 is integrally connected to each side of sliding bar 66 and surface 63 for reinforcing sliding bar 66. Sliding bar 66 fits within a rectangular groove 112 formed within needle guard 52. Sliding bar 66 engages groove 112 in a sliding telescopic in and out motion, and prevents needle guard 52 from rotating, but maintains needle assembly 50 in coaxial alignment with needle guard 52 at all times.

Once attached to luer lock syringe 85, only casing 54 rotates in a partial circular movement while in operation. The rest of the device remains substantially in a constant linear telescoping alignment. A locking tab memory lever or spring finger 98, also has a slight down and up movement during use, which will be more fully explained hereafter.

A planar end surface 68 at the end of sliding bar 66 abuts a rectangular groove surface 110 at the end of groove 112, and prevents further backward movement of needle guard 52 on sliding bar 66 during an injection. Needle shaft 72 is made of any desired length, so long as needle point 70 does not protrude from the end of needle guard 52 at an opening 106. Needle shaft 72 can also be made of any gauge or thickness, so long as it slides easily within a needle guard shaft circular lumen 108, contained in a needle guard tubular nose portion 102. Lumen 108 is also sized to receive needle shaft 72 according to the size of needle shaft 72. Hollow needle point 70 is sharp to penetrate a patient's skin for injection of a fluid medication or aspiration of a body substance. Needle point 70 is typical of conventional hypodermic syringe needles.

COMPRESSION SPRING

Figure 6:
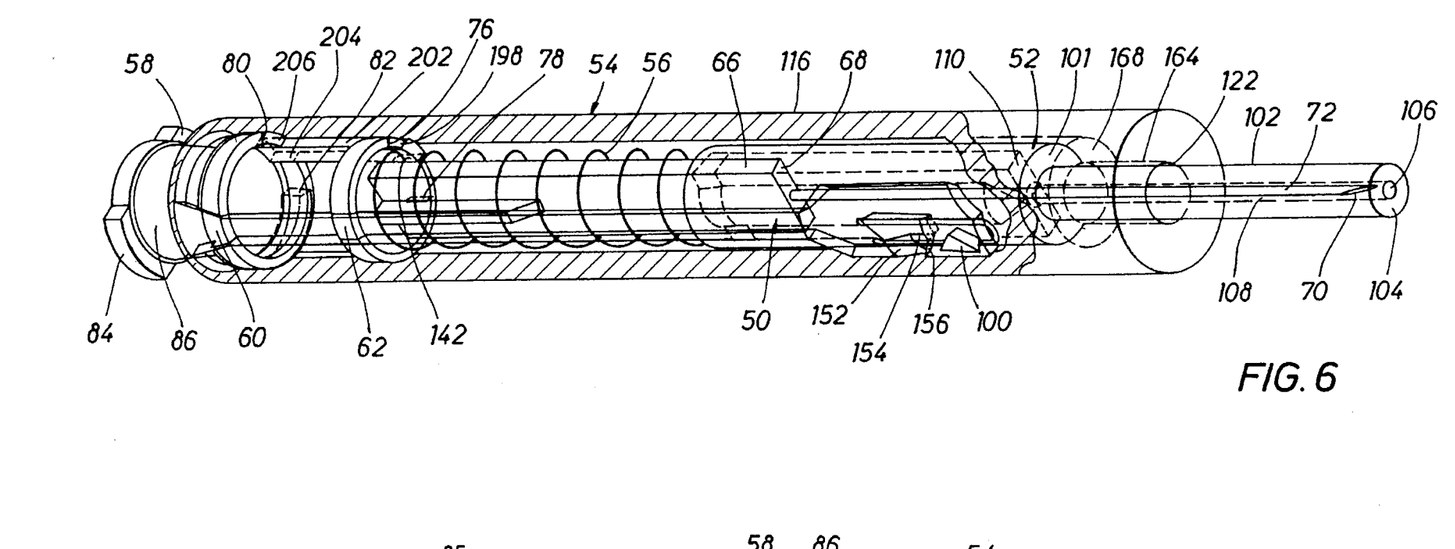
FIG. 6 is an isometric view with certain parts broken away of the assembled self sheathing needle shown in FIG. 1.

In between needle assembly 50 and needle guard 52 is a compression spring 56 shown in FIGS. 1 and 6. The length and diameter of spring 56 is made such that there is always a slight forward urging force applied to an end 91 of needle guard 52. The diameter of spring 56 is also made such that it fits within casing 54 without binding when in operation, and surrounds sliding bar 66.

Figure 8:
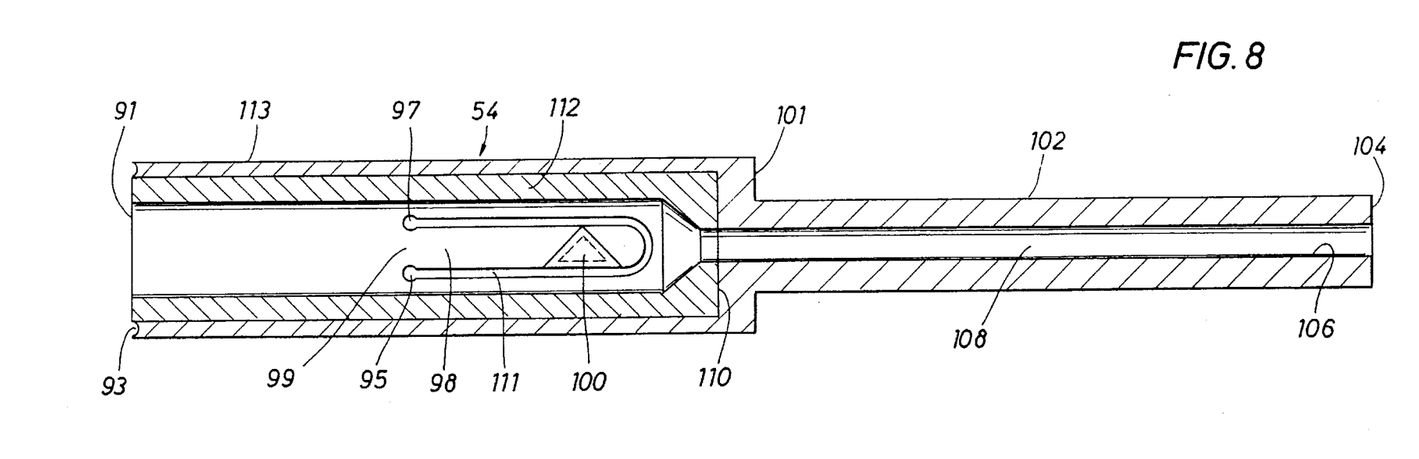
FIG. 8 is a front plan view of the needle guard member shown in FIG. 1.

The thickness and diameter of spring 56 is sized to fit into a stabilizing groove 93 cut into end 91 of needle guard 52 as shown particularly in FIG. 8 to hold spring 56 in proper alignment within the device. Spring 56 is further made of a light tension, which is enough to continuously push needle guard 52 forward at all times, but which will not cause the patient any undue discomfort during injection.

A front end 90 of spring 56 pushes on end 91 of needle guard 52 from within stabilizing groove 93 shown in FIG. 8. A rear end 88 of spring 56 abuts against surface 63 of needle assembly 50, and is thus held in position between needle assembly 50 and needle guard 52.

NEEDLE GUARD

Figure 3:
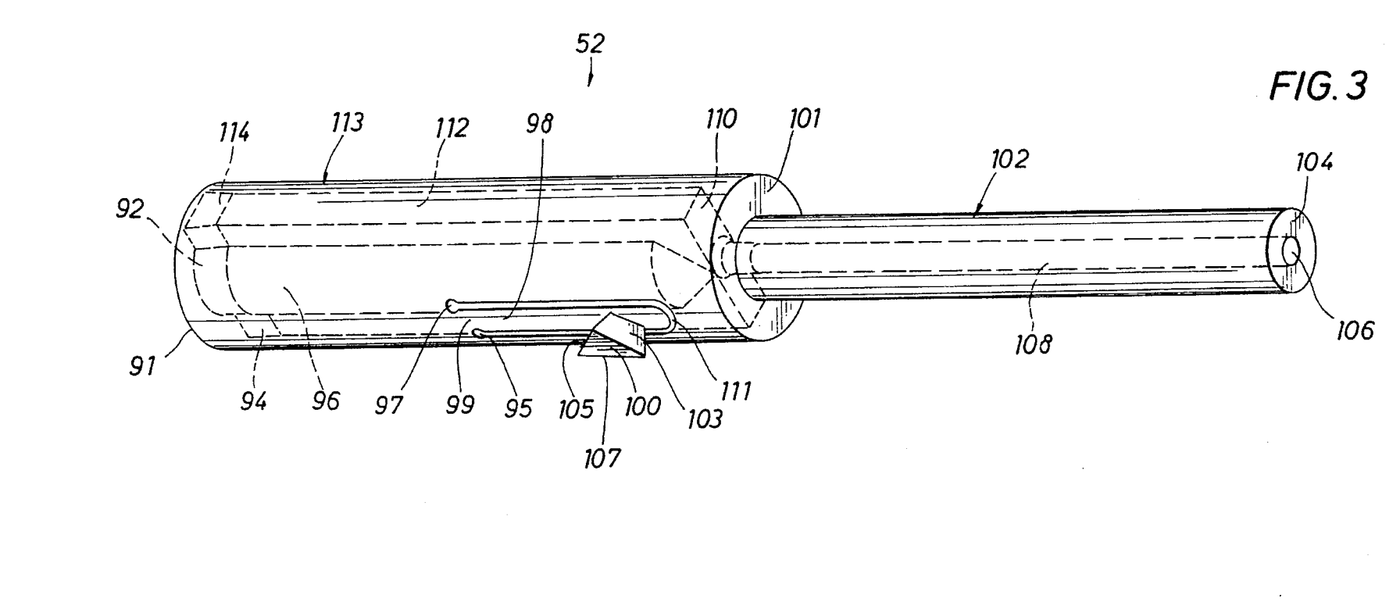
FIG. 3 is an enlarged isometric view of the needle guard member of the invention shown in FIG. 1.

Needle guard 52 comprises two main body portions, a large diameter rear cylindrically shaped hollow body portion 113 and integral resilient small diameter front cylindrically shaped hollow body portion or nose portion 102. Body portion 102 extends through an opening 122 in casing 54 and slides back and forth along annular surface 164 defining opening 122 during operation. Needle guard 52 abuts an internal circular shoulder surface 168 of casing 54 in an extended position. Body portion 113 has a cylindrical outer surface between annular end surfaces 91 and 101. A cutout portion 111 communicating with central bore 96 of hollow body portion 113 has integral resilient finger or memory lever 98 therein as shown particularly in FIG. 3. Memory lever 98 is integrally formed with body 113 at a junction 99, and is made out of a resilient material such as plastic, that has properties of springing back to its original shape. Memory lever or finger 98 also follows the curvature and is flush with body portion 113 when at rest.

A pair of C shaped stress openings 95 and 97 are located at either end of cutout portion 111, and distribute the stress placed on junction 99 as memory lever 98 is flexed over a wide area of needle guard 52, instead of only in the immediate vicinity of junction 99.

Figure 4:
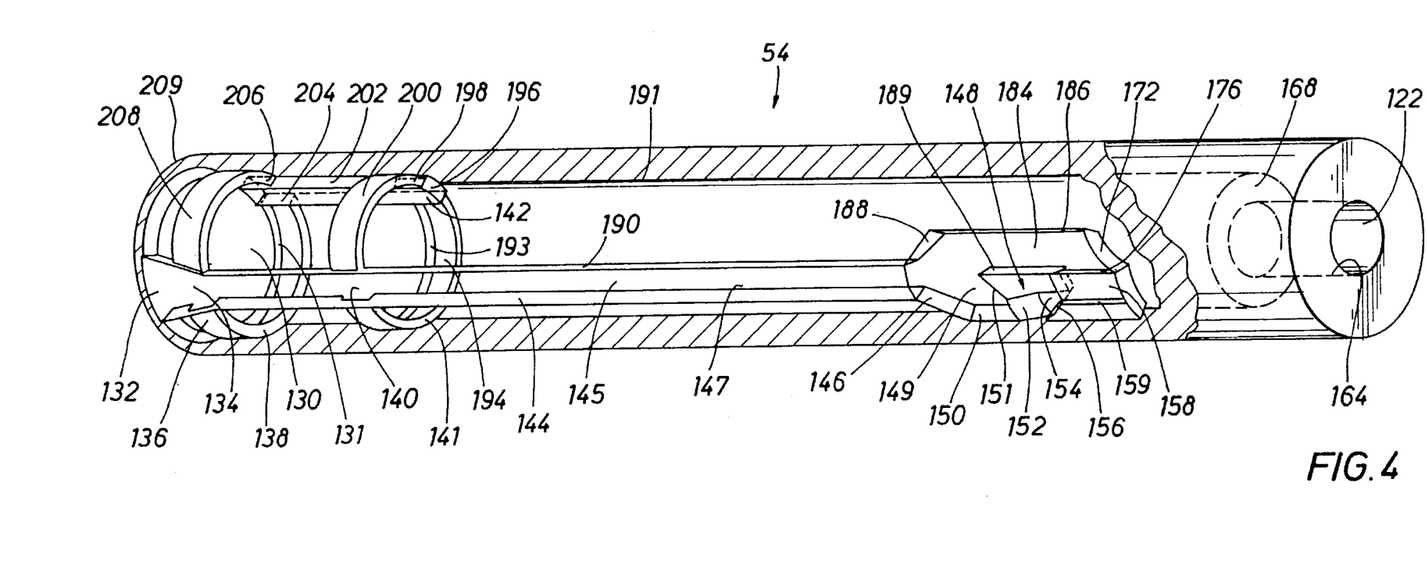
FIG. 4 is an enlarged isometric cutaway view of the casing member of my self sheathing needle shown in FIG. 1.

At the free end of memory level 98 opposite junction 99 is a triangular shaped locking tab 100, which protrudes outwardly from the outer surface of body portion 113, in order to engage with a locking tab track 145 which is formed in an inside wall 191 of casing 54, and is shown in FIG. 4.

Although in the drawings locking tab 100 is represented by a triangular shape, a round circular shape will function in a satisfactory manner, and thus locking tab 100 does not necessarily have to be a triangular shape for adequate functioning of my self sheathing needle. Also locking tab 100 and track 145 could be reversed on casing 54 and needle guard 52.

The sides of locking tab 100 are formed at an inclined acute angle with the surface of memory lever 98. The bottom of locking tab 100 which is integrally formed with memory lever 98 is thus smaller than the top of locking tab 100. The inclined acute angles of locking tab 100 match similar inclined acute angles formed on the engaging surfaces of locking tab track 145. This configuration serves to pull locking tab 100 into and against the locking tab track 145 during operation, and prevents disengagement of the locking tab 100 from locking tab track 145. The only way that locking tab 100 can become disengaged from locking tab track 145 would be under an extreme twisting force strong enough to break the entire device. Such a force could only be encountered in a normal patient injection during attachment of the invention to a syringe. However, under such extreme force, the threads of the syringe should strip before the device would fail. If the device did fail under these conditions, the device would jam and become inoperable, thus preventing a needle stick injury.

Proceeding further now, at the open end of groove 112 in needle guard 52 are a pair of enlarged extension areas 114 and 94 of a trapezoidal shape. Extension areas 114 and 94 are tapered to guide sliding bar 66 into groove 112. Body portion 113 has a bore 96 which starts in a tapered fashion at area 92, extends through body portion 113, and then tapers to needle shaft lumen 108.

During operation, needle point 70 passes through opening 106 at a front end 104 of front body portion 102. However, because of the constant forward urging of spring 56 against end 91 of needle guard 52, front end 104 always stays in contact with whatever is being injected, whether medication vial or patient, and needle point 70 is thus never exposed to the outside. Therefore, needle point 70 is unable to inflict any accidental needle stick injury.

CASING

Casing 54 is shown in FIG. 1 in an exploded view and in FIG. 4 in an enlarged view. Casing 54 has a tubular generally cylindrical body having an open outer end 130, an outside perimeter 209, and a smaller opening 122 at the opposite inner end. Outer peripheral surface 116 extends between open end 130 and smaller opening 122. A direction arrow 128 and an instruction text 118 may be printed on the outside of casing 54, towards the back portion if desired. A second direction arrow 126 and an instruction text 120 may also be printed on casing 54 if desired towards the front portion. End surface 104 with opening 122 substantially in the middle forms the forward end of casing 54. Casing 54 is preferably made of one piece construction, but may, if desired, be formed of a pair of longitudinal half sections which are joined together.

Referring now to FIG. 4, outside perimeter 209 forms the back end of casing 54. An elongated locking tab track 145 begins with a flared opening 132 near outside perimeter 209. A circular bearing track 208 and a circular bearing track 136 are formed in an inside wall 191 of casing 54. Bearing tracks 208 and 136 are sized and shaped to receive bearing 60 in a rotational sliding engagement. Bearing track 136 intersects track 145 at an opening 134. Bearing track 208 also intersects track 145 similarly at opening 134. The opposite end of bearing track 208 terminates at the intersection of track 208 with a longitudinally extending rotational stop bar 202 at a rotational stop surface 206. Rotational stop surface 206 also forms one end of track 208. Stop surface 206 limits the rotational movement of casing 54 when engaged by safety stop 82 during operation.

Rotational stop bar 202 projects from inside wall 191, extends between track 208 and track 200 in a lengthwise direction, and terminates at end 196. The intersection of track 200 with stop bar 202 forms a rotational stop surface 198. Track 200 and a rotational beating track 194 intersect track 145 at an opening 140. Track 200 and track 194 are sized and shaped to receive bearing 62 in a sliding rotational engagement, and are formed in wall 191 of casing 54. A bearing track wall 141 and a bearing track wall 139 prevent bearing 62 and bearing 60 from any forward movement inside casing 54. Similarly, a bearing track wall 193 and a bearing track wall 131 prevent backward movement of bearing 62 and bearing 60 within casing 54. Thus, once assembled, casing 54 is only allowed to rotate a predetermined amount, such as 60 degrees, about the central longitudinal axis of the device. Track 194 terminates at a rotational stop surface 142, which is formed by the intersection of track 194 with stop bar 202.

A side track wall 144 and a side track wall 190 of track 145 extend from opening 134 until they reach an inclined flat track wall 146 and an inclined flat track wall 188 respectively. Walls 146 and 188 are formed at an inclined angle, to approximately match the inclination of surface 98 of locking tab 100. Walls 146 and 188 form part of track 145 in which locking tab 100 travels.

Figure 5:
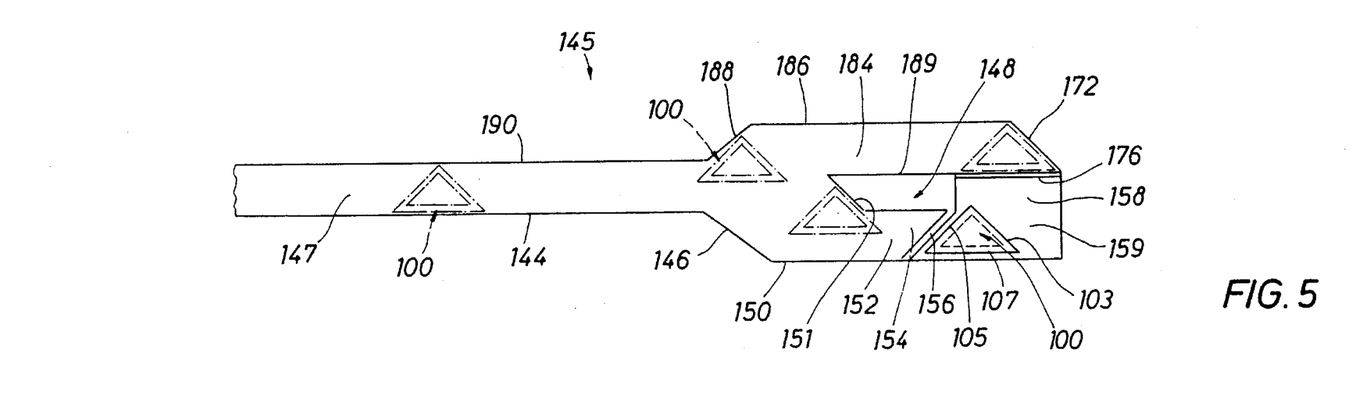
FIG. 5 is a schematic view of the locking tab track, and locking tab illustrating the different positions of the locking tab during operation.

Elongate track section 147 as shown also schematically in FIG. 5 leads to an enlarged track area in which a cam lug generally indicated at 148 has a plurality of surfaces for guiding locking tab 100 between an extended locked position of needle guard 52 and an extended unlocked position of needle guard 52 to permit retraction of needle guard 52. The enlarged track area includes a track surface 150 which continues the track for locking tab 100 from a retracted position of needle guard 52 and is substantially parallel to the longitudinal axis of the device. A surface 151 on lug 148 is near the middle of track 145 and has an inclination angle similar to surface 103 of locking tab 100. Surface 151 articulates with locking tab 100 and forces it into a channel 149 as seen in FIG. 4 and FIG. 5. The forward force of spring 56 then forces locking tab 100 to continue to move forward, and up a locking ramp 152 on lug 148.

After passing up ramp 152 and over an adjacent lug portion 154, locking tab 100 passes over an edge surface 156 of lug portion 154. After passing over edge surface 156 of lug portion 154, memory lever 98 then forces locking tab 100 radially outwardly toward the outer surface 116 of casing 54 in track 145 away from the central longitudinal axis of casing 54. Locking tab 100 is now in the locked position of needle guard 52, as it can only go slightly forward, but is prevented from going rearwardly as blocked by edge surface 156 on lug portion 154 if needle guard 52 is forced in a backward direction. Edge surface 156 is formed at an inclined angle to match a rear surface 105 of locking tab 100. In the locked position, locking tab 100 will remain in channel 159, as seen in FIG. 4 and FIG. 5.

In the assembled position of the self sheathing needle of this invention as shown in FIG. 6, casing 54 having an outer cylindrical body may be easily gripped. Needle assembly 50 has a sliding bar 66 fitting within internal grooves 112 of needle guard 52 thereby to define coacting guide members to permit sliding longitudinal movement of needle guard 52 relative to needle assembly 50 but blocking any relative rotative movement between needle guard 52 and needle assembly 50. Needle guard 52 and needle assembly 50 are received within outer casing 54 which is supported on arcuate bearings 60 and 62 for limited relative rotation between locked and unlocked extended positions of needle guard 52. Stop bar 202 on casing 54 abuts stops 78, 82 on bearings 60, 62 in a locked extended position of needle guard 52 to permit retraction of needle guard 52. Syringe 85 is attached to projecting lugs 58, 84 on needle assembly 50 as shown in FIG. 7. Thus, casing 54 is normally rotated relative to syringe 85, needle assembly 50, and needle guard 52. However, syringe 85, needle assembly 50, and needle guard 52 may be rotated relative to casing 54, if desired.

In operation with syringe 85 attached for an intramuscular injection and needle guard 52 in an extended locked position, casing 54 is rotated counterclockwise until a "click" is heard. During rotation, locking tab 100 moves sideways through channel 159, and up a side ramp 158 on cam lug 148. At edge surface 176 of ramp 158, locking tab 100 is then forced radially outward by memory lever 98 into channel 184, and is prevented from going back into channel 159 by edge 176. A base surface 107 of locking tab 100 abuts edge 176 and prevents any clockwise rotation of casing 54. A wall 172 of track 145 is formed at an inclined angle to approximately match surface 103 of locking tab 100, and prevents locking tab 100 from moving forward while located in channel 184. An upper surface 189 of cam lug 148 blocks locking tab 100 on one side, and a track wall 186 blocks locking tab 100 on the other side, only allowing locking tab 100 to travel along the longitudinal axis of the device, while in channel 184. As the front end 104 of needle guard 52 is pressed against the patient during injection, locking tab 100 travels along channel 184. Surface 105 of locking tab 100 then engages wall 188 of track 145. Wall 188 then forces locking tab 100 to travel into an elongated section 147 of track 145, and backward further up track 145, as needle 72 is injected.

Figure 9A:
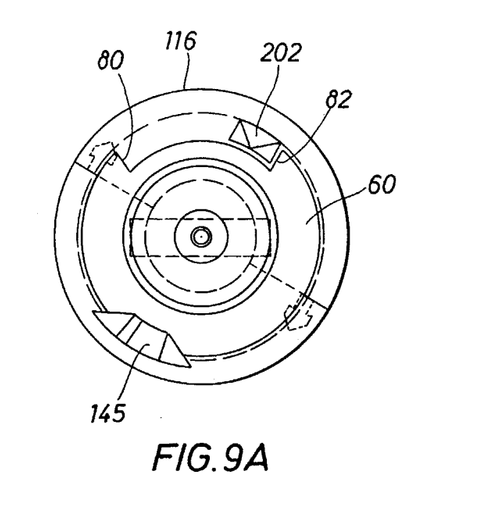
FIG. 9A is an end view of the casing member and needle assembly.
Figure 9B:
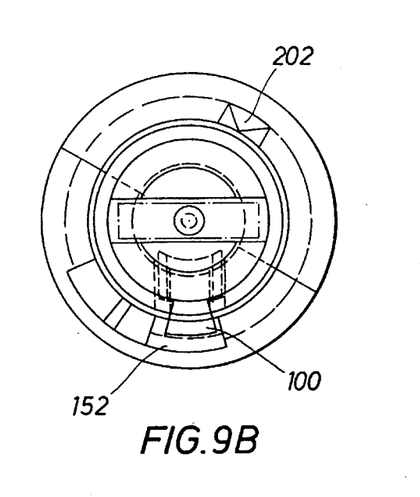
FIG. 9B is an end view of the casing member and needle guard member illustrating the locking tab immediately prior to engaging the ramp for moving to a locked position.
Figure 9C:
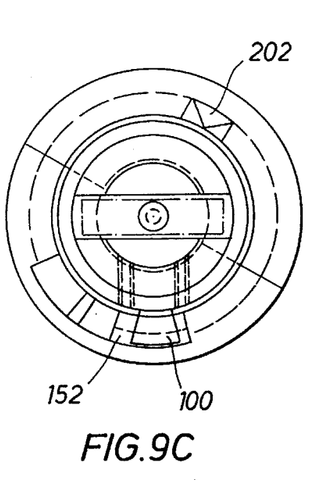
FIG. 9C is an end view of the casing member and needle guard member similar to FIG. 9B but showing the locking tab in a locked position behind the ramp.

As needle 72 is withdrawn from the patient, locking tab 100 then travels back down track 145, engages surface 151 of lug 148, and is forced into channel 149 of track 145. Due to the forward force exerted by spring 56, locking tab 100 is then forced up ramp 152, and memory lever 98 is simultaneously flexed radially inwardly to allow locking tab 100 to ascend ramp 152. Locking tab 100 now continues in a forward direction, transverses ramp 152 while sliding over a surface 154, and finally snaps back radially outwardly into place in channel 158, after transversing surface edge 156. Memory lever 98 also assumes its original shape flexing outwardly again at the same time. Reference is made also to FIGS. 9A, 9B and 9C which illustrate movement of locking tab 100. Locking tab 100 is now again in the locked position, and a needle stick injury is not possible. As a result of the present invention, this protection is accomplished simultaneously as the needle is being withdrawn from the patient.

While the present invention has been described for use with a syringe for injection of a fluid, this invention may be used for blood collection. The invention is particularly adapted for use with a blood collection system which utilizes a double-ended blood collection needle with a threaded fitting such as shown in U.S. Pat. No. 5,181,524 dated Jan. 26, 1993, the entire disclosure of which is incorporated by this reference.

While the preferred embodiment of the present invention has been illustrated in detail, it is apparent that modifications and adaptations of the preferred embodiment will occur to those skilled in the art. However, it is to be expressly understood that such modifications and adaptations are within the spirit and scope of the present invention as set forth in the following claims.

I claim:

1. A self sheathing needle device comprising:

a needle assembly including a base on one end thereof and a hollow needle extending from said base for the injection or aspiration of a fluid;

an elongate hollow needle guard member movable relative to said needle assembly between an extended locked position, an extended unlocked position, and a plurality of retracted unlocked positions;

an elongate outer casing member surrounding and receiving said needle guard member in a telescoping relation and rotatably connected at one end to said base, said needle guard member extending outwardly from an opposed end of said casing member;

means within said elongate outer casing member to bias said needle guard member continuously toward one of said extended positions;

means mounting said outer casing member and said needle guard member for relative rotation and for relative longitudinal movement; and coacting guide means on said outer casing member and said needle guard member to control relative movement between said casing member and said needle guard member for guiding said needle guard member between said locked and unlocked positions, said coacting guide means including a resilient locking element on one member movable resiliently in a generally radial direction relative to the other member for locking said needle guard member in said extended locked position.

2. A self sheathing needle device as set forth in claim 1 wherein:

said coacting guide means includes a guide for said locking element mounted on said other member for guiding said needle guard member between said locked and unlocked positions, said needle guard member moving from said extended locked position to said extended unlocked position only upon rotation of said casing member relative to said needle guard member.

3. A self sheathing needle device as set forth in claim 2 wherein:

said guide comprises a track in which said locking element 15 mounted for relative sliding movement and for relative rotational movement, said track including a ramp for caming said locking element in a generally radial direction for locking and unlocking of said locking element.

4. A self sheathing needle device as set forth in claim 2 wherein:

said resilient locking element comprises a resilient finger having an extended free end thereof and a locking tab on said extended free end.

5. A self sheathing needle device as set forth in claim 4 herein:

said guide comprises a track on which said locking tab is mounted for sliding movement and for relative rotative movement, said track including a ramp for caming said locking element in a generally radial direction for locking of said locking tab.

6. A self sheathing needle device comprising:

a needle assembly including a hollow needle for the injection or aspiration of a fluid;

an elongate hollow needle guard member movable between an extended locked position, an extended unlocked position, and a plurality of retracted unlocked positions;

an elongate casing member surrounding said needle guard member in a telescoping relation;

means to bias said needle guard member continuously toward one of said extended positions;

means mounting said casing member and said needle guard member for relative rotation and for relative longitudinal movement; and coacting guide means on said casing member and said needle guard member to control relative movement between said casing member and said needle guard member for guiding said needle guard member between said locked and unlocked positions, said coacting guide means including a resilient locking element on one member movable in a generally radial direction relative to the other member for locking said needle guard member in said extended locked position;

said needle assembly having a base on one end thereof for securing said hollow needle with said needle extending therefrom and terminating at a free outer end;

said hollow needle guard member having an inner guide receiving said base in a nonrotative relation while permitting sliding movement of said hollow needle guard member along said base in a longitudinally extending axial relation, said needle guard member extending beyond said free outer end of said needle in locked and unlocked extended positions.

7. A self sheathing needle device as set forth in claim 6 wherein:

said hollow needle guard member comprises a large diameter rear cylindrical hollow portion and an integral small diameter forward cylindrical hollow portion, said large diameter cylindrical portion including said inner guide and movable along said base of said needle assembly; and said means to bias comprises a coil spring extending about said base of said needle assembly and engaging said large diameter cylindrical portion of said needle guard member for continuously urging said needle guard member to one of said extended positions.

8. A self sheathing needle device as set forth in claim 6 wherein:

said base includes an outer hub portion operable for releasable connection to a medical device, said hub portion including a bearing member engaging said casing member and supporting said casing member for relative rotative movement upon rotation of said casing member.

9. A self sheathing needle device as set forth in claim 8 wherein:

a pair of spaced stops are provided adjacent said bearing member for limiting relative rotative movement of said casing member.

10. A self sheathing needle device as set forth in claim 7 wherein:

said hollow casing member has a large diameter opening adjacent an outer end to receive said large diameter portion of said needle guard member therein and a small diameter opening adjacent an inner end to receive said small diameter cylindrical portion of said needle guard member, said needle guard member mounted for sliding longitudinal movement within said hollow casing member.

11. A self sheathing needle device as set forth in claim 9 wherein:

said casing member has a bearing member coacting with said bearing member on said hub portion of said base, said casing member including a stop member coacting with said pair of spaced stops on said bearing member of said needle assembly for limiting rotational movement of said casing member.

12. A self sheathing needle device comprising:

an integral needle assembly having a base on one end thereof and a hollow needle extending from said base terminating at a free outer end;

an elongate hollow needle guard member movable between an extended locked position, an extended unlocked position, and a plurality of retracted unlocked positions; said hollow needle guard member including a large diameter rear cylindrical portion and an integral small diameter forward cylindrical portion;

an outer hollow cylindrical casing member having a large diameter end opening at an outer end thereof and a small diameter end opening at an inner end thereof, said needle guard member fitting within said outer casing member in telescoping relation for relative sliding movement with said small diameter cylindrical portion extending through said small diameter end opening;

a coil spring extending about said base of said needle assembly and engaging said large diameter cylindrical portion of said needle guard member for continuously urging said needle guard assembly to one of said extended positions; and coacting guide means on said outer casing member and said needle guard member to permit relative rotation of said members between said extended locked position and said extended unlocked position, said needle guard member receiving said hollow needle and projecting beyond said free outer end of said needle in said extended locked position and said extended unlocked position.

13. A self sheathing needle device as set forth in claim 12 wherein:

said coacting guide means includes a resilient finger on one member having a locking tab on said finger; and a track on the other member in which said locking tab is mounted for sliding movement and for relative rotative movement.

14. A self sheathing needle device as set forth in claim 13 wherein:

said track includes a ramp for caming said locking tab in a generally radial direction for locking and unlocking of said needle guard member.

15. A self sheathing needle device as set forth in claim 13 wherein:

said base includes an outer hub portion operable for releasable connection to a medical device, said hub portion including an outer arcuate bearing member supporting said casing member for relative rotative movement upon rotation of said casing member.

16. A self sheathing needle device as set forth in claim 15 wherein:

a pair of spaced stops are provided adjacent said bearing member for limiting relative rotative movement of said casing member.

17. A self sheathing needle device as set forth in claim 15 wherein:

said casing member has an inner arcuate bearing member coacting with said outer bearing member on said hub portion of said base, said casing member including a stop for coacting with said pair of spaced stops on said bearing member of said needle assembly for limiting rotational movement of said casing member relative to said needle guard member.

18. A self sheathing needle device comprising:

an integral needle assembly having a base on one end thereof and a hollow needle extending from said base terminating at a free outer end;

an elongate hollow needle guard member movable between an extended locked position, an extended unlocked position, and a plurality of retracted unlocked positions; said hollow needle guard member including a large diameter rear portion and an integral small diameter forward portion;

an outer casing member having an end opening at an inner end thereof, said needle guard member fitting within said outer casing member in telescoping relation for relative sliding movement with said small diameter forward portion extending through said end opening;

means continuously urging said needle guard assembly to one of said extended positions;

first coacting guide means on said outer casing and said needle guard member to permit relative manual rotation of said members, said needle guard member receiving said hollow needle and projecting beyond said free outer end of said needle in said extended locked position and said extended unlocked position; and second coacting guide means on said base of said needle assembly and said needle guard member to permit sliding longitudinal movement of said needle guard member relative to said base.

19. A self sheathing needle device as set forth in claim 18 wherein:

said base includes an outer hub portion operable for releasable connection to a medical device, said hub portion including an arcuate bearing member supporting said casing member for relative rotative movement upon rotation of said casing member; and a pair of spaced stops are provided adjacent said bearing member for limiting relative rotative movement of said casing member.

20. A self sheathing needle device as set forth in claim 19 wherein:

said casing member has an inner arcuate bearing member coacting with said outer bearing member on said hub portion of said base, said casing member including a stop for coacting with said pair of spaced stops on said bearing member of said needle assembly for limiting rotational movement of said casing member relative to said needle guard member.

* * * * *